United States Patent [19]

Ürogdi et al.

[11] 4,371,534
[45] Feb. 1, 1983

[54] N4-SUBSTITUTED TETRAHYDRO-1,2,4-OXADIAZIN-5-ONE DERIVATIVES HAVING ANTICONVULSIVE ACTIVITY AND PHARMACEUTICAL COMPOSITIONS CONTAINING THEM

[75] Inventors: László Ürodgi; Agnes Patthy nee Lukats; Lajos Kisfaludy; Ernö Moravcsik Helga Tüdos nee Feur; László Ötuös; Zsuzsanna Tegyei; Èra Pálost; Ádám Sarkari; László Szporny, all of Budapest, Hungary

[73] Assignee: Richter Gedeon Vegyeszeti Gyar RT., Budapest, Hungary

[21] Appl. No.: 335,342

[22] Filed: Dec. 29, 1981

[30] Foreign Application Priority Data

Dec. 31, 1980 [HU] Hungary ............................ 3165/80

[51] Int. Cl.³ .................. A61K 31/535; C07D 273/04
[52] U.S. Cl. .......................... 424/248.55; 424/248.57; 424/248.58; 544/68
[58] Field of Search ................... 544/68; 424/248.55, 424/248.57, 248.58

[56] References Cited

U.S. PATENT DOCUMENTS 3,574,201 4/1971 Breuer ............................ 544/68 X

OTHER PUBLICATIONS

Farge et al., Chemical Abstracts, vol. 87 (1977) 53402k.

Primary Examiner—Richard Raymond
Attorney, Agent, or Firm—Karl F. Ross

[57] ABSTRACT

The invention relates to new tetrahydro-1,2,4-oxadiazin-5-one derivatives having a CNS activity. More particularly, the invention concerns new N⁴-substituted tetrahydro-1,2,4-oxadiazin-5-ones of the formula (1)

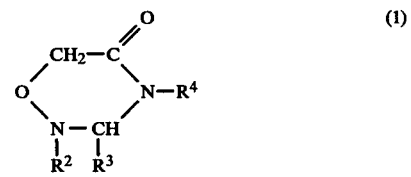

wherein
$R^2$ is benzyloxycarbonyl or alkylcarbonyl containing 1 to 4 carbon atoms in the alkyl moiety, preferably acetyl;
$R^3$ is phenyl optionally substituted with 1 to 3 lower alkoxy groups; and
$R^4$ is an aliphatic or cyclic alkyl group having 1 to 11 carbon atoms, hydroxymethyl, halomethyl or acyloxymethyl.

According to another aspect of the invention there are provided processes for the preparation of compounds of formula (1). Still another aspect of the invention is a pharmaceutical composition which comprises as active ingredient a compound of formula (1).

5 Claims, No Drawings

N4-SUBSTITUTED TETRAHYDRO-1,2,4-OXADIAZIN-5-ONE DERIVATIVES HAVING ANTICONVULSIVE ACTIVITY AND PHARMACEUTICAL COMPOSITIONS CONTAINING THEM

The invention relates to new $N^4$-substituted tetrahydro-1,2,4-oxidiazin-5-one derivative having anticonvulsive activity. More particularly, the invention concerns new tetrahydro-1,2,4-oxidiazin-5-one derivatives of the formula (I)

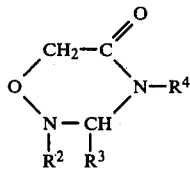  (I)

wherein
$R^2$ is benzyloxycarbonyl or alkylcarbonyl containing 1 to 4 carbon atoms in the alkyl moiety, preferably acetyl;
$R^3$ is phenyl optionally substituted with 1 to 3 lower alkoxy groups; and
$R^4$ is an aliphatic or cyclic alkyl group having 1 to 11 carbon atoms, hydroxymethyl, halomethyl or acyloxymethyl.

According to another aspect of the invention there are provided processes for the preparation of compounds of the formula (I).

Still another aspect of the invention is a pharmaceutical composition which comprises as active ingredient a pharmaceutically effective amount of a compound of formula (I) with at least one pharmaceutically inert carrier or diluent.

Substituted derivatives of tetrahydro-1,2,4-oxadiazine have only lately become known in the art. The synthesis of such compounds was first reported by Calcagno et al. [J. Org. Chem. 39, 162 (1974)]. The authors prepared 4-aroyl-tetrahydro-1,2,4-oxadiazines by cycloaddition of a nitrone and a corresponding 1-aroyl-aziridine. Recently F. G. Riddel et al. [Heterocycles 9, 267 (1978); Tetrahedron 35, 1391 (1979)] have prepared a tetrahydro-1,2,4-oxadiazine skeleton by condensing an N-alkyl-O-(methylamino)-ethyl-hydroxyl-amine with formaldehyde. The biological activity of those compounds was not reported nor were described tetrahydro-1,2,4-oxadiazine-derivatives containing an oxo group in the 5-position.

We have found that the new compounds of the formula (I), wherein $R^2$, $R^3$ and $R^4$ have the same meaning as defined above, can easily be prepared by (a) condensing an α-aminooxy-carboxylic acid amide of the formula (II)

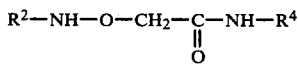  (II)

wherein
$R^2$ has the same meaning as defined above and
$R^4$ is an aliphatic or cyclic alkyl group having 1 to 11 carbon atoms,
with benzaldehyde optionally substituted in the ring by one to three lower alkoxy groups, in an aprotic or protic medium, in the presence of an acid, to afford compounds of the formula (I), in which $R^4$ is an aliphatic or cyclic alkyl group having 1 to 11 carbon atoms; or (b) reacting a tetrahydro-1,2,4-oxadiazin-5-one derivative of the formula (III)

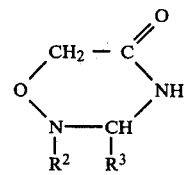  (III)

wherein $R^2$ and $R^3$ are as defined above, with a compound of the formula (IV)

$$X\text{-}R^4 \qquad (IV)$$

wherein
X is a reactive ester residue, preferably halogen
$R^4$ is an aliphatic or cyclic alkyl group having 1 to 11 carbon atoms,
in the presence of a base or with formaldehyde, in the presence of a base, preferably an organic tertiary amine, and if desired, converting a compound of the formula (I) obtained, in which $R^4$ is hydroxymethyl into a corresponding compound of the formula (I), in which $R^4$ is acyloxymethyl or halogenmethyl by reacting with an acylating agent, preferably an organic carboxylic acid halide or carboxylic acid anhydride, or a halogenating agent, preferably thionyl halide, and if desired, replacing an $R^2$ benzyloxycarbonyl group in a compound of the formula (I) prepared by any of process variants (a) and (b) by an acetyl group, preferably by hydrogenation and reaction with an acetylating agent.

In the definition of $R^3$ the term "lower alkoxy" is used to refer to alkoxy groups having 1 to 4, preferably 1 or 2 carbon atoms, e.g. methoxy.

The starting compounds of formula (II) are known in the art [see the U.S. Pat. No. 3,733,358 and the corresponding British Pat. No. 1.329.590]. Tetrahydro-1,2,4-oxadiazin-5-one derivatives of the formula (III) are new compounds, which can be prepared by reacting acylaminooxyacetic acid amides of the formula (II), in which $R^4$ is hydrogen with aromatic aldehydes in a aprotic or protic medium. This process is the subject of our commonly assigned concurrently filed copending application Ser. No. 335,341.

As an aprotic solvent in process variant (a) preferably hydrocarbons, more preferably aromatic hydrocarbons, e.g. benzene and/or toluene can be used. To improve solubility if desired, a small amount of butyl acetate can be added to these solvents. As an acid catalyst mineral acids or, more preferably, camphor-10-sulfonic acid can be employed. It should be noted that the use of the latter acid for similar purposes has not been described in the literature. The reaction is preferably performed at the boiling temperature of the solvent and water is continuously eliminated by a suitable water separator.

As a protic medium preferably a 1:1 (v./v.) mixture of acetic acid and acetic anhydride is employed to which mineral acids or camphor-10 sulfonic acid may be added. In this case the reaction is carried out at room temperature (15° C.–25° C.).

In both aprotic and protic solvents the reaction takes a considerably long time, its completion requires several days.

The progress of the reaction can be monitored by thin layer chromatography. As soon as the reaction is complete, the solvent is eliminated, the residue is dissolved in a water-immiscible organic solvent, the solution is washed with an acidic or alkaline aqueous solution, dried and evaporated to dryness. If desired, the end product obtained as a residue may be purified by recrystallization.

According to process variant (b) a starting compound of the formula (III), which is unsubstituted on the nitrogen in the 4-position is preferably reacted with an alkyl halide containing an alkyl moiety corresponding to the alkyl group to be attached to the 4-position, under reaction conditions, conventionally employed for N-alkylation, in the presence of an acid binding agent. To attach a hydroxymethyl group to the 4-position of the 1,2,5-oxadiazine ring the hydroxy-methylation is preferably carried out with an aqueous formaldehyde solution, in the presence of an organic tertiary base, preferably triethyl amine. The 4-hydroxymethyl derivative obtained is a very appropriate starting material for preparing further 4-substituted derivatives, e.g. by replacing the hydroxyl by halogen or carrying out an O-acylation. These per se known reactions are also carried out under conventional reaction conditions. The 4-hydroxymethyl derivative can for example be reacted with thionyl chloride or an acyl halide corresponding to the desired end product, in the presence of an acid binding agent, for example triethyl amine.

The 2-benzyloxycarbonyl group of a compound of the formula (I) prepared by any of the above methods, can easily be replaced by an acetyl group under conventional conditions. For example a compound of the formula (I) containing a benzyloxycarbonyl group in place of $R^2$, in which $R^4$ is as defined above, can be subjected to catalytic hydrogenation in acetic anhydride or in a mixture of acetic anhydride and dimethyl formamide. In this case the acetylation of the 2-nitrogen atom takes place simultaneously with the elimination of the benzyloxycarbonyl group. Alternatively, the benzyloxycarbonyl group may be eliminated in a neutral medium, by catalytic hydrogenation and the compound obtained may subsequently be acylated.

The isolation of the end product from the reaction mixture is carried out essentially in the same way as in process variant (a).

The pharmaceutical activity of the new compounds according to the invention was tested by conventional animal tests. Tests were performed on CFLP (LATI) mice of both sexes weighing 18 to 22 g. each, in groups of 10. Test compounds were suspended in a 5% aqueous "Tween 80" solution and the suspension was administered orally, through a probe. When testing anticonvulsive activity 20 mg./kg. doses, while in the tests concerning neurotoxic activity 80 mg/kg. doses were employed. The induced effect was measured one hour after administration by the following methods:

1. Test of anticonvulsive activity (a) Maximum electroshock (MES):
According to the method of E. A. Swinyard et al. [J. Pharmacol. 106, 319 (1952)] test animals were shocked by a corneal electrode (20 mA, 0.2 sec.). On the stimulation 100% of the control animals reacted by a tonic, extensor spasm of the lower limbs. Absence of this phenomena was considered a protection due to the treatment.

(b) inhibition of spasm induced by pentetrazole (PTT)
According to the method of Cr. N. Everett and R. K. Richards [J. Pharmacol. Exp. Therap. 81, 402 (1944)] 125 mg./kg. of pentatrazole (pentamethylene tetrazole) were administrated to the animals subcutaneously. One hour after administration the animals were observed. Absence of the clonic spasm (Kl) and the tonic, extensor spasm of lower limbs (TE) was considered a protection due to the administration of test compounds.

2. Test of neurotoxic activity

Muscle coordination (RR) on mice

Change of the coordinated muscular movement was tested according to W. J. Kinnard and C. F. Carr [Brit. J. Pharmacol, 121, 354 (1957)], on a rotating rod (diameter: 20 mm., frequency: 12/min.). Normal trained animals are able to remain on the rotating rod for about 120 seconds. One hour after administration it was determined what percent of the test animals showed muscle incoordination, i.e. the number of animals falling down from the rotating rod within 120 seconds was determined and expressed in percentage of the control animals.

3. Acute toxicity

Toxicity of the compounds was examined by administration of various single doses. Evaluation was made 14 days after administration. The $LD_{50}$-values were calculated on the basis of the number of animals that died in 14 days by probite analysis, by means of a TPA/101 computer.

As a reference substance in the above tests diphenyl hydantoine and 3-methyl-5-phenylhydantoine were used. The results obtained are shown in the following table.

| Compounds of formula (I) | | | | PTT | | | $LD_{50}$ mg/kg |
|---|---|---|---|---|---|---|---|
| $R^2$ | $R^3$ | $R^4$ | MES | TE | Cl | RR | p.o. |
| $CH_3CO-$ | $C_6H_5-$ | $CH_3-$ | 40 | 20 | 0 | 20 | 800 |
| $CH_3CO-$ | $C_6H_5-$ | $C_2H_5-$ | 0 | 20 | 0 | 20 | 800 |
| $CH_3CO-$ | $C_6H_5-$ | $n-C_6H_{13}-$ | 0 | 40 | 0 | 0 | 800 |
| $CH_3CO-$ | $C_6H_5-$ | $HOCH_2-$ | 60 | 40 | 0 | 20 | 800 |
| $CH_3CO-$ | $C_6H_5$ | $ClCH_2-$ | 40 | 0 | 0 | 40 | 800 |
| $CH_3CO$ | $C_6H_5$ | $CH_3COOCH_2$ | 70 | 60 | 0 | 40 | 800 |
| $CH_3CO-$ | $C_6H_5$ | $C_6H_5-COO-CH_2-$ | 40 | 70 | 0 | 40 | 800 |
| $CH_3CO-$ | $C_6H_5$ | 3,4,5-trimethoxy-benzoyloxymethyl- | 30 | 0 | 0 | 0 | 800 |
| diphenylhydantoine | | | 90 | 80 | 0 | 70 | 279 |
| 3-methyl-5-ethyl-5-phenylhydantoine | | | 10 | 50 | 0 | 50 | 476 |

The data set forth in the above table clearly show that the tested representatives of compounds of formula (I) have excellent anticonvulsive activity. These compounds induce a lower muscle incoordination than the hydantoine derivatives used for comparision and their toxicity is also lower, accordingly their therapeutic which is considerably greater than that of the known compounds with similar activity. Therefore, the new compounds of the formula (I) can be used for treating epilepsy more successfully than the hydantoine derivatives widely used for this purpose.

The components of the formula (I) can be used in the therapy in the form of pharmaceutical compositions containing an effective amount of these active ingredients in admixture with organic or inorganic carriers or diluents suitable for enteral or parenteral administration. The compositions may be finished as tablets, injections, dilute or concentrated suspensions or emulsions or other conventional formulations. These formulations are prepared by conventional techniques of the pharmaceutical industry.

The pharmaceutical compositions according to the invention generally contain about 30 to 100 mg. of active ingredient per dose unit. Their administration in human therapy includes oral or parenteral administration, preferably in the form of intravenous injections. The actual doses depend on the disease to be treated, on the condition of the patient, route of administration and the desired effect. Generally daily doses between 200 and 600 mg. are employed.

Further details of the invention are illustrated by the following non-limiting examples. The abbreviations used in the examples are entirely in line wth the IUPAC rules.

The melting points of the compounds disclosed in the Examples were determined in an apparatus by dr. Tottali (Büchi). The thin layer chromatograms were prepared on "Kieselgel G" (Merck) silica gel plates according to Stahl, which were sensitized to ultraviolet radiation. For preparing the chromatograms the following solvent mixture was used:

(A): 1:1 mixture of benzene and acetone

The thin layer chromatograms were developed by one or more of the following methods:
1. u.v. irradiation at 254 nm
2. treatment with iodine vapor
3. tolidine/potassium iodide spray, after chlorination.

The structure of the compounds prepared was analyzed by elemental analysis, and on the basis of the IR and NMR spectra. The IR spectra were determined on a "Perkin-Elmer 257" apparatus and the NMR spectra were recorded on a "Varian EM-60" apparatus.

The evaporation of the reaction mixtures was carried out on a "Rotavapor R" (Büchi) vacuum evaporator at a temperature not exceeding 50° C.

EXAMPLE 1

2-Benzyloxycarbonyl-3-phenyl-4-methyl-tetrahydro-1,2,4-oxadiazin-5-one (method a)

A mixture of 2.29 g (9.6 mmoles) of N-(benzyloxycarbonyl)-aminooxy-N'-methyl acetamide, 2.0 ml. (19.8 mmoles) of benzaldehyde and 0.3 g of camphor-10-sulfonic acid in 40 ml. of benzene is refluxed in a flask equipped with a Marcusson water separator for 3 days, while the water formed is continuously eliminated. The progress of the reaction is monitored by thin layer chromatography and as soon as the reaction is complete the reaction mixture is evaporated to dryness and the residue is crystallized from a mixture of 5 ml. of ether and 20 ml. of hexane. 1.65 g. (50%) of 2-benzyloxycarbonyl-3-phenyl-4-methyl-tetrahydro-1,2,4-oxadiazin-5-one are obtained, melting at 82° to 83° C.; $R_f^A = 0.7$.

Analysis for $C_{18}H_{18}N_2O_4$ (molecular weight: 326.35): calculated: C=66.25%, H 5.56%, N 8.58%; found: C=66.27% H 5.30%, N 8.52%.

IR spectrum (KBr): 1730 (C=O), 1665 (C=O, amide), 1410 (ring), 745, 700 (aromatic) $cm^{-1}$.

NMR spectrum (DMSO-d/6, CDCl$_3$, TMS) ppm: 2.83 s (—CH$_3$), 4.58 s (—CH$_2$—C=O), 5.28 s (—CH$_2$—C$_6$H$_5$), 6.49 s (=CH-), 7.25–8.6 m (10H, aromatic).

EXAMPLE 2

2-Benzyloxycarbonyl-3-phenyl-4-methyl-tetrahydro-1,2,4-oxadiazin-5-one (method b)

To a suspension of 0.24 g. (5 mmoles) of a 50% sodium hydride in 10 ml. of dry tetrahydrofurane a solution of 1.56 g. (5 mmoles) of 2-benzyloxycarbonyl-3-phenyltetrahydro-1,2,4-oxadiazin-5-one in 10 ml. of dry tetrahydrofurane is added, under vigorous stirring. The suspension obtained is stirred at a temperature of 0° C. for 20 minutes, whereupon a solution of 0.35 ml. (5.6 moles) of methyl iodide in 5 ml. of tetrahydrofurane is added dropwise. The mixture is stirred at room temperature overnight, whereupon several drops of acetic acid are added and the solvent is evaporated under reduced pressure. The residue is dissolved in 10 ml. of chloroform, the solution is shaken with 3 ml. of water, 3 ml. of a 1 N hydrochloric acid solution and finally 3 ml. of a 1 N sodium hydrocarbonate solution and is then evaporated. The residue is crystallized from a mixture of 2 ml. of isopropanol and 5 ml of hexane to give 0.25 g. of 2-benzyloxycarbonyl-3-phenyl-4-methyl-tetrahydro-1,2,4-oxadiazin-5-one (15%), melting at 82° to 83° C. $R_f = 0.7$. The further physical properties of the product are identical with those of the product of Example 1.

EXAMPLE 3

3-Benzyloxycarbonyl-3-phenyl-4-ethyl-tetrahydro-1,2,4-oxadiazin-5-one (method c)

0.65 g. (2.5 mmoles) of N-benzyloxycarbonyl)-aminooxy-N'-ethyl-acetamide and 0.4 ml. (4 mmoles) of benzaldehyde are dissolved in a mixture of 2.5 ml. of acetic acid and 0.3 ml. of acetic anhydride, whereupon 0.12 ml. of a concentrated sulfuric acid solution is added to the solution, which is then allowed to stand at room temperature for one hour. Thereafter 0.7 g. of sodium acetate trihydrate are added to the mixture and it is evaporated to dryness. The residue is dissolved in 10 ml. of ethyl acetate, the solution is extracted with 3 ml. of a 1 N aqueous sodium hydrocarbonate solution, 3 ml. of a 1 N aqueous hydrochloric acid solution and finally with two 3-ml. portions of water, whereupon it is dried over anhydrous sodium sulfate and evaporated to dryness. As a residue 0.69 g. (75%) of 2-benzyloxycarbonyl-3-phenyl-4-ethyl-tetrahydro-1,2,4-oxadiazin-5-one are obtained. The product is practically chromatographically pure; $R_f^A = 0.8$. This product may be used as a starting material in the reaction according to Example 4 without further purification.

EXAMPLE 4

2-Acetyl-3-phenyl-4-ethyl-tetrahydro-1,2,4-oxadiazin-5-one (method d)

0.69 g. (2 mmoles) of 2-benzyloxycarbonyl-3-phenyl-4-ethyl-tetrahydro-1,2,4-oxadiazin-5-one are dissolved in 7 ml. of acetic anhydride, 0.1 g. of a 5%, palladium-on-activated carbon catalyst are added and hydrogen gas is bubbled through the mixture at room temperature under vigorous stirring. The progress of hydrogenation is monitored by thin layer chromatography. As soon as the reaction is complete, the catalyst is filtered off, the filtrate is evaporated to dryness under reduced pressure and the residue is recrystallized from 1 ml. of ethanol. 0.41 g. (82%) of 2-acetyl-3-phenyl-4-ethyl-tetrahydro-1,2,4-oxadiazin-5-one are obtained, melting at 130° C. to 132° C. $R_f^A=0.6$.

Analysis for $C_{13}H_{16}N_2O_3$ (molecular weight: 248.26): calculated: C 62.88%, H 6.49%, N 11.27%; found: C 62.25%, H 6.37%, N 11.12%.

IR spectrum (KBR): 1645 (C=O), 1274 (amide III), 740, 693 (aromatic) cm$^{-1}$.

NMR spectrum (CDCl$_3$, TMS) ppm: 1.16+(—CH$_2$—$\underline{CH_3}$), 2.13 s (CH$_3$CO—), 2.86 and 3.9 m (>N—CH$_2$—$\underline{CH_3}$), 4.6 s (—CH$_2$—CO—). 6.7 s(>CH—), 7.40 s (5H, aromatic).

EXAMPLE 5

2-Acetyl-3-phenyl-4-hydroxymethyl-tetrahydro-1,2,4-oxadiazin-5-one

To a solution of 1.1 g. (5 mmoles) of 2-acetyl-3-phenyl-tetrahydro-1,2,4-oxadiazin-5-one in 10 ml. of tetrahydrofurane 1 ml. of triethyl amine and 0.4 ml. of a 37% aqueous formaldehyde solution are added. The mixture is allowed to stand at room temperature overnight and is then evaporated to dryness. The residue is triturated with diethyl ether and the product is isolated by filtration. 1.16 g. (93%) of 2-acetyl-3-phenyl-4-hydroxymethyl-tetrahydro-1,2,4-oxadiazin-5-one are obtained, melting at 123° to 126° C. $R_f^A=0.5$.

Analysis for $C_{12}H_{14}N_2O_4$ (molecular weight: 250.25): calculated: C 57.59%, H 6.64%, N 11.19%, found: C 57.49%, H 6.03%, N 10.99%.

IR spectrum (KBr): 3330, 1053 (—OH), 1675 (>C=O), 1648 (>C=O, amide), 753, 710 (aromatic) cm$^{-1}$.

NMR spectrum (DMSO-d$_6$+CDCl$_3$, TMS) ppm: 2.0 s (—CH$_3$), 4.7 AB quadruplet (—CH$_2$—CO—), 4.1 2xd and 5.5 2xd (>N—CH$_2$—OH), 6.0+(—OH), 7.0 s (>CH—), 7.5 s (5H, aromatic).

EXAMPLE 6

2-Acetyl-3-phenyl-4-acetoxymethyl-tetrahydro-1,2,4-oxadiazin-5-one (method e)

To a solution of 1.0 g. (4 mmoles) of 2-acetyl-3-phenyl-4-hydroxymethyl-tetrahydro-1,2,4-oxadiazin-5-one in 10 ml. of dry tetrahydrofurane 0.72 ml. of dry triethyl amine are added. The solution is cooled to 0° C. and 0.36 ml. (0.40 g., 5 mmoles) of acetyl chloride are added dropwise at this temperature. The mixture is stirred at room temperature for two hours, the precipitated triethyl amine hydrochloride is filtered off and the filtrate is evaporated to dryness. The residue is dissolved in 10 ml. of ethyl acetate, the solution is shaken with 3 ml. of a 1 N aqueous sodium hydrocarbonate solution, 3 ml. of a 1 N aqueous hydrochloric acid solution and finally with two 3-ml. portions of water, whereupon it is dried with anhydrous sodium sulfate and evaporated to dryness. The residue is recrystallized from a mixture of 3 ml. of diethyl ether and 6 ml. of n-hexane. 0.90 g. (77%) of 2-acetyl-3-phenyl-4-acetoxymethyl-tetrahydro-1,2,4-oxadiazin-5-one are obtained, melting at 75° C. to 76° C. $R_f^A=0.7$.

Analysis for $C_{14}H_{16}N_2O_5$ (molecular weight: 292.28): calculated: C 57.52%, H 5.52%, N 9.58%; found: C 57.30%, H 5.56%, N 9.49%.

IR spectrum (KBr): 1740 (>C=O ester), 1680 (>C=O amide), 1210 (C—O—C) 750-700 (aromatic) cm$^{-1}$. NMR spectrum (DMSO-d$_6$, TMS) ppm: 2.0 s (—CH$_3$), 2.13 s (—CH$_3$), 4.66 s (—CH$_2$—CO—), 4.96 and 5.46 AB quadruplet (>N—CH$_2$—), 6.9 s (>CH—), 7.46 s (5H, aromatic).

EXAMPLE 7

2-Acetyl-3-phenyl-4-chloromethyl-tetrahydro-1,2,4-oxadiazin-5-one 0.5 g. (2 mmoles) of 2-acetyl-3-phenyl-4-hydroxymethyltetrahydro-1,2,4-oxadiazin-5-one are refluxed in 3 ml. of thionyl chloride for one hour. The solution is evaporated to dryness under reduced pressure. The residue is triturated with diethyl ether cooled to 0° C. and the product is filtered off and is subsequently recrystallized from a mixture of 2 ml. of chloroform and 6 ml. of n-hexane. 0.28 g. (53%) of 2-acetyl-3-phenyl-4-chloromethyl-tetrahydro-1,2,4-oxadiazin-5-one are obtained, melting at 171° to 172° C.; $R_f^A=0.7$.

Analysis for $C_{12}H_{13}N_2O_3$ (molecular weight: 26.8.70): calculated: C 53.64%, H 4.88%, N 10.43%, Cl 13.20% found: C 53.10%, H 4.78%, N 9.77%, Cl 13.57%.

IR spectrum (KBr): 1683, 1665 (>C=O), 753, 698 (aromatic) 680 (>C—Cl) cm$^{-1}$.

NMR spectrum (CDCl$_3$, TMS) ppm: 2.13 s (—CH$_3$), 4.67 s (—CH$_2$—CO—), 4.41 and 6.91 AB quadruplet (>N—CH$_2$Cl), 6.93 s (—CH—), 7.46 s (5H, aromatic).

The compound set forth in the following Table were prepared according to any of the methods "a" to "e" illustrated by the above examples. In the Table in addition to the substituent meanings the physical constants of compounds, the methods used for their preparation, the yields and the solvent(s) used for the recrystallization are also indicated.

| Example No. | R$^2$ | R$^3$ | R$^4$ | Mp °C. | R$_f^A$ | Process varient | Yield % | Solvent used for recrystallization |
|---|---|---|---|---|---|---|---|---|
| 8 | C$_6$H$_5$—CH$_2$—O—CO— | —C$_6$H$_5$ | CH$_3$ | 82–83 | 0.7 | b | 50 | ether/n-hexane |
| 9 | C$_6$H$_5$—CH$_2$—O—CO— | 2,5-(CH$_3$O)$_2$—C$_6$H$_3$— | CH$_3$— | 98–100 | 0.9 | b | 25 | ethanol |
| 10 | CH$_3$CO— | C$_6$H$_5$— | CH$_3$ | 100–101 | 0.5 | b$^x$ | 20 | — |
| 11 | CH$_3$CO— | C$_6$H$_5$— | n-C$_3$H$_7$— | 74–76 | 0.6 | a + b | 45 | |
| 12 | CH$_3$CO— | C$_6$H$_5$— | i-C$_3$H$_7$— | 102 | 0.6 | c + d | 39 | ethanol |
| 13 | CH$_3$CO— | C$_6$H$_5$— | cyklopropyl | 165 | 0.6 | a + d | 30 | ethanol |
| 14 | CH$_3$CO— | C$_6$H$_5$— | n-hexyl | oil | 0.7 | a + d | 32 | — |
| 15 | CH$_3$CO— | C$_6$H$_5$— | cyklohexyl | 124–126 | 0.6 | a + d | 38 | ethylacetate/n-hexane |
| 16 | CH$_3$CO— | C$_6$H$_5$— | n-octyl | oil | 0.7 | c + d | 45 | — |
| 17 | CH$_3$CO— | C$_6$H$_5$— | undecyl | oil | 0.8 | a + d | 41 | — |

| Example No. | $R^2$ | $R^3$ | $R^4$ | Mp °C. | $R_f^x$ | Process varient | Yield % | Solvent used for recrystallization |
|---|---|---|---|---|---|---|---|---|
| 18 | $CH_3CO-$ | $C_6H_5-$ | benzoyloxymethyl | 83–84 | 0.7 | e | 75 | ether/n-hexane |
| 19 | $CH_3CO-$ | $C_6H_5-$ | 3,45-trimethoxy-benzoyloxymethyl | 150–151 | 0.7 | e | 72 | ethanol |

$^x$column chromatography on silica gel, 1:1 mixture of benzene and acetone

We claim:

1. A tetrahydro-1,2,4-oxadiazin-5-one of the formula (1)

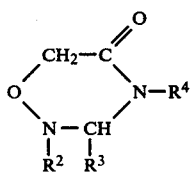

wherein
  $R^2$ is benzyloxycarbonyl or alkylcarbonyl containing 1 to 4 carbon atoms in the alkyl moiety;
  $R^3$ is phenyl optionally substituted by 1 to 3 lower alkoxy groups;
  $R^4$ is an aliphatic or cyclic alkyl group having 1 to 11 carbon atoms, hydroxymethyl, halogenmethyl or acyloxymethyl.

2. Compounds as claimed in claim 1, in which in the formula (1) $R^2$ is acetyl, $R^3$ and $R^4$ are as defined in claim 1.

3. The compound defined in claim 1 selected from the group consisting of:

(a) 2-acetyl-3-phenyl-4-methyl-tetrahydro-1,2,4-oxadiazin-5-one;
(b) 2-acetyl-3-phenyl-4-ethyl-tetrahydro-1,2,4-oxadiazin-5-one;
(c) 2-acetyl-3-phenyl-4-n-hexyl-tetrahydro-1,2,4-oxadiazin-5-one;
(d) 2-acetyl-3-phenyl-4-hydroxymethyl-tetrahydro-1,2,4-oxadiazin-5-one;
(e) 2-acetyl-3-phenyl-4-chloromethyl-tetrahydro-1,2,4-oxadiazin-5-one;
(f) 2-acetyl-3-phenyl-4-acetoxymethyl-tetrahydro-1,2,4-oxadiazin-5-one;
(g) 2-acetyl-3-phenyl-4-benzoyloxymethyl-tetrahydro-1,2,4-oxadiazin-5-one; and
(h) 2-acetyl-3-phenyl-4(3,4,5-trimethoxy-benzoyloxymethyl)-tetrahydro-1,2,4-oxadiazin-5-one.

4. An anticonvulsive method of treatment which comprises the step of administering to an animal subject in need of said treatment a pharmaceutically effective amount of the compound defined in claim 1.

5. A anticonvulsive composition which comprises as active ingredient a pharmaceutically effective amount of a compound of formula (1), in which $R^2$, $R^3$ and $R^4$ are as defined in claim 1, in association with at least one pharmaceutically inert carrier or diluent.

* * * * *